US00PP21402P2

(12) United States Plant Patent
Eveleens

(10) Patent No.: US PP21,402 P2
(45) Date of Patent: Oct. 19, 2010

(54) *GERBERA* PLANT NAMED 'FLOGLADES'

(50) Latin Name: *Gerbera jamesonii*
Varietal Denomination: Floglades

(75) Inventor: Jan Leendert Eveleens, Aalsmeer (NL)

(73) Assignee: Florist de Kwakel B.V., Aalsmeer (NL)

( * ) Notice: Subject to any disclaimer, the term of this patent is extended or adjusted under 35 U.S.C. 154(b) by 0 days.

(21) Appl. No.: 12/454,022

(22) Filed: May 11, 2009

(51) Int. Cl.
*A01H 5/00* (2006.01)

(52) U.S. Cl. ..... Plt./357

(58) Field of Classification Search ..... Plt./357
See application file for complete search history.

*Primary Examiner*—June Hwu
(74) *Attorney, Agent, or Firm*—C. A. Whealy

(57) ABSTRACT

A new and distinct cultivar of *Gerbera* plant named 'Floglades', characterized by its compact, upright and uniformly mounding plant habit; freely flowering habit; semi-double type inflorescences with ray florets that are initially red purple in color and with development becoming white and red purple in color; and upright, strong and relatively short scapes.

1 Drawing Sheet

Botanical designation: *Gerbera jamesonii.*
Cultivar denomination: 'Floglades'.

BACKGROUND OF THE INVENTION

The present invention relates to a new and distinct cultivar of *Gerbera* plant, botanically known as *Gerbera jamesonii* and hereinafter referred to by the name 'Floglades'.

The new *Gerbera* plant is a product of a planned breeding program conducted by the Inventor in De Kwakel, The Netherlands. The objective of the breeding program is to create new compact container *Gerbera* cultivars with numerous inflorescences, good garden performance and attractive ray and disc floret coloration.

The new *Gerbera* plant originated from a cross-pollination in March, 2003 in De Kwakel, The Netherlands of *Gerbera jamesonii* 'Lira-Lode', not patented, as the female, or seed, parent with *Gerbera jamesonii* 'Moana', not patented, as the male, or pollen, parent. The new *Gerbera* was discovered and selected by the Inventor as a single flowering plant within the progeny of the stated cross-pollination in a controlled greenhouse environment in De Kwakel, The Netherlands during the spring of 2004.

Asexual reproduction of the new *Gerbera* plant by tissue culture in a controlled environment in De Kwakel, The Netherlands since the summer of 2004 has shown that the unique features of this new *Gerbera* plant are stable and reproduced true to type in successive generations.

SUMMARY OF THE INVENTION

Plants of the new *Gerbera* have not been observed under all possible environmental conditions. The phenotype may vary somewhat with variations in environment such as temperature and light intensity, without, however, any variance in genotype.

The following traits have been repeatedly observed and are determined to be the unique characteristics of 'Floglades'. These characteristics in combination distinguish 'Floglades' as a new and distinct cultivar of *Gerbera:*

1. Compact, upright and uniformly mounding plant habit.
2. Freely flowering habit.

3. Semi-double type inflorescences with ray florets that are initially red purple in color and with development becoming white and red purple in color.
4. Upright, strong and relatively short scapes.

Plants of the new *Gerbera* differ from plants of the female parent, 'Lira-Lode', in the following characteristics:

1. Plants of the new *Gerbera* are more compact than plants of 'Lira-Lode'.
2. Plants of the new *Gerbera* have shorter scapes than plants of 'Lira-Lode'.
3. Ray florets of plants of the new *Gerbera* are pink to white and red purple in color whereas ray florets of 'Lira-Lode' are pink and white in color.

Plants of the new *Gerbera* differ from plants of the male parent, 'Moana', in the following characteristics:

1. Plants of the new *Gerbera* are more compact than plants of 'Moana'.
2. Plants of the new *Gerbera* have shorter scapes than plants of 'Moana'.
3. Plants of the new *Gerbera* have semi-double type inflorescences whereas plants of 'Moana' have single type inflorescences.
4. Ray florets of plants of the new *Gerbera* are pink to white and red purple in color whereas ray florets of plants of 'Moana' are pink in color.

Plants of the new *Gerbera* can be compared to plants of the *Gerbera jamesonii* 'Everlast Pink', not patented. Plants of the new *Gerbera* differ from plants of 'Everlast Pink' in the following characteristics:

1. Plants of the new *Gerbera* are more uniform in growth habit than plants of 'Everlast Pink'.
2. Plants of the new *Gerbera* have larger inflorescences than plants of 'Everlast Pink'.
3. Plants of the new *Gerbera* have semi-double type inflorescences whereas plants of 'Everlast Pink' have single type inflorescences.
4. Ray florets of plants of the new *Gerbera* are pink to white and red purple in color whereas ray florets of plants of 'Everlast Pink' are pink in color.

5. Plants of the new *Gerbera* have thicker scapes than plants of 'Everlast Pink'.

BRIEF DESCRIPTION OF THE PHOTOGRAPH

The accompanying photograph illustrates the overall appearance of the new *Gerbera* plant. This photograph shows the colors as true as it is reasonably possible to obtain in colored reproductions of this type. Colors in the photograph may differ slightly from the color values cited in the detailed botanical description which accurately describe the colors of the new *Gerbera* plant. The photograph comprises a side perspective view of a typical flowering plant of 'Floglades' grown in a container.

DETAILED BOTANICAL DESCRIPTION

The aforementioned photograph and following observations and measurements describe plants grown in a glass-covered greenhouse during the winter in De Kwakel, The Netherlands and under conditions and practices which approximate those generally used in commercial container *Gerbera* production. During the production of the plants, day temperatures ranged from 19° C. to 26° C. and night temperatures ranged from 16° C. to 18° C. Rooted young tissue-cultured plants were planted in 19-cm containers and had been growing for six months when the photograph and description were taken. In the following description, color references are made to The Royal Horticultural Society Colour Chart, Fifth Edition, 2007, except where general terms of ordinary dictionary significance are used.

Botanical classification: *Gerbera jamesonii* 'Floglades'.

Parentage:

*Female, or seed, parent.*—*Gerbera jamesonii* 'Lira-Lode', not patented.

*Male, or pollen, parent.*—*Gerbera jamesonii* 'Moana', not patented.

Propagation:

*Type.*—By tissue culture.

*Time to initiate roots.*—About 2.5 weeks at temperatures of 20° C.

*Time to produce a rooted young plant.*—About five to six weeks at temperatures of 20° C. to 26° C.

*Root description.*—Fibrous; white in color.

*Rooting habit.*—Moderate branching; dense.

Plant description:

*Appearance.*—Herbaceous semi-double type *Gerbera*; compact, upright and uniformly mounding plant habit; arching leaves arranged in basal rosettes; dense and bushy habit; moderately vigorous growth habit.

*Plant height.*—About 63.5 cm.

*Plant width.*—About 74 cm.

Foliage description:

*Arrangement.*—Alternate, simple.

*Length.*—About 45 cm.

*Width.*—About 20.5 cm.

*Shape.*—Runcinate; lanceolate to narrowly elliptic in outline.

*Apex.*—Obtuse to abruptly obtuse.

*Base.*—Acuminate.

*Margin.*—Pinnately lobed with coarse and irregular sinuses, lobes divergent; undulate.

*Texture, upper surface.*—Sparsely pubescent.

*Texture, lower surface.*—Moderately pubescent; woolly.

*Venation pattern.*—Pinnate.

*Color.*—Developing leaves, upper surface: Close to 141A. Developing leaves, lower surface: Close to 137B to 137C. Fully expanded leaves, upper surface: Close to N137B; venation, close to 144B to 144C. Fully expanded leaves, lower surface: Between 137D and 138B; venation, close to 144B.

*Petioles.*—Length: About 7.5 cm. Diameter: About 5.9 mm. Texture, upper surface: Sparsely pubescent. Texture, lower surface: Moderately pubescent. Color, upper and lower surfaces: Close to 144B.

Inflorescence description:

*Appearance.*—Semi-double type inflorescence form with narrowly oblanceolate-shaped ray florets; solitary inflorescences borne on upright, strong and relatively short scapes above the foliar plane; ray and disc florets arranged acropetally on a capitulum.

*Fragrance.*—None detected.

*Flowering season.*—Plants begin flowering about four months after planting and flower from early spring to the end of the summer in outdoor gardens in The Netherlands. Plants flower year-round under greenhouse conditions.

*Inflorescence longevity.*—Inflorescences last about two weeks on the plant; inflorescences persistent.

*Quantity of inflorescences.*—Freely flowering habit with about seven open and developing inflorescences per plant at one time. Inflorescence bud: Height: About 1.9 cm. Diameter: About 4 cm. Shape: Oblate. Color: Close to 144B.

*Inflorescence size.*—Diameter: About 14.4 cm. Depth (height): About 4.1 cm. Diameter of disc: About 4.3 cm. Receptacle height: About 9 mm. Receptacle diameter: About 9 mm. Receptacle color: Close to NN155C.

*Ray florets.*—Orientation: Initially upright, then about 75° from vertical. Outer whorls of ray florets: Length: About 6.2 cm. Width: About 1.3 cm. Inner whorls of ray florets: Length: About 3.8 cm to 4.8 cm. Width: About 4 mm to 6 mm. Shape: Narrowly oblanceolate. Apex: Obtuse. Base: Cuneate. Margin: Entire. Texture, upper and lower surfaces: Smooth, glabrous; longitudinally ridged.

Number of outer whorls of ray florets per inflorescence: About 110 arranged in about three whorls. Color: When opening, upper surface, outer whorls of ray florets: Close to N66C. When opening, upper surface, inner whorl of ray florets: Close to N66A. When opening, lower surface, outer and inner whorls of ray florets: Close to 2D. Fully opened, upper surface, outer whorls of ray florets: Close to 155D; longitudinal stripes and towards the margins, close to 62D; with development, red purple color of the longitudinal stripes and margins become fainter. Fully opened, upper surface, inner whorl of ray florets: Close to 63A. Fully opened, lower surface, outer and inner whorls of ray florets: Close to 158C.

*Disc florets.*—Arrangement: Massed at center of receptacle. Shape: Tubular, fused. Apex: Acute. Base: Fused. Margin: Entire. Length: About 1.8 cm. Width: About 5 mm. Texture, upper and lower surfaces: Smooth, glabrous. Number of disc florets per inflorescence: About 500. Color, immature: Apex: Close to 63A. Mid-section and base: Close to 158B. Color, mature: Apex: Close to 63B. Mid-section and base: Close to 158B.

*Pappus.*—Quantity per floret: About 50. Length: About 8 mm. Diameter: Less than 1 mm. Texture: Soft. Color: Between N77A and 187A.

*Phyllaries.*—Number of phyllaries per inflorescence: About 96 in about three whorls. Length: About 1.4 cm. Width: About 3 mm. Shape: Lanceolate. Apex: Acute. Base: Cuneate. Margin: Entire. Texture, upper surface: Smooth, glabrous. Texture, lower surface: Densely tomentose. Color, upper surface: Close to 143A; apices, close to 144A. Color, lower surface: Close to 137B; apices, close to 143B.

*Scapes.*—Length: About 48 cm. Diameter: About 8 mm. Angle: Erect. Strength: Strong. Texture: Densely tomentose. Color: Close to 144B; towards the apex, close to 137B.

*Reproductive organs.*—Androecium (present on disc florets only): Quantity per floret: Two. Filament length: About 6 mm. Filament color: Close to NN155C. Anther shape: Lanceolate. Anther length: About 4 mm. Anther color: Close to 12B. Pollen amount: Moderate. Pollen color: Close to 12A. Gynoecium (present on ray and disc florets): Quantity per floret: One. Pistil length: About 1.1 cm. Stigma shape: Rounded; curved. Stigma color: Close to 155D. Style length: About 1 cm. Style color: Close to NN155C. Ovary color: Close to 145D.

*Seed/fruit.*—Seed and fruit production has not been observed.

Disease/pest resistance: Resistance to pathogens and pests common to *Gerberas* has not been observed on plants of the new *Gerbera* grown under commercial conditions.

Temperature tolerance: Plants of the new *Gerbera* have been observed to tolerate temperatures from about 1° C. to about 35° C.

It is claimed:

1. A new and distinct *Gerbera* plant named 'Floglades' as illustrated and described.

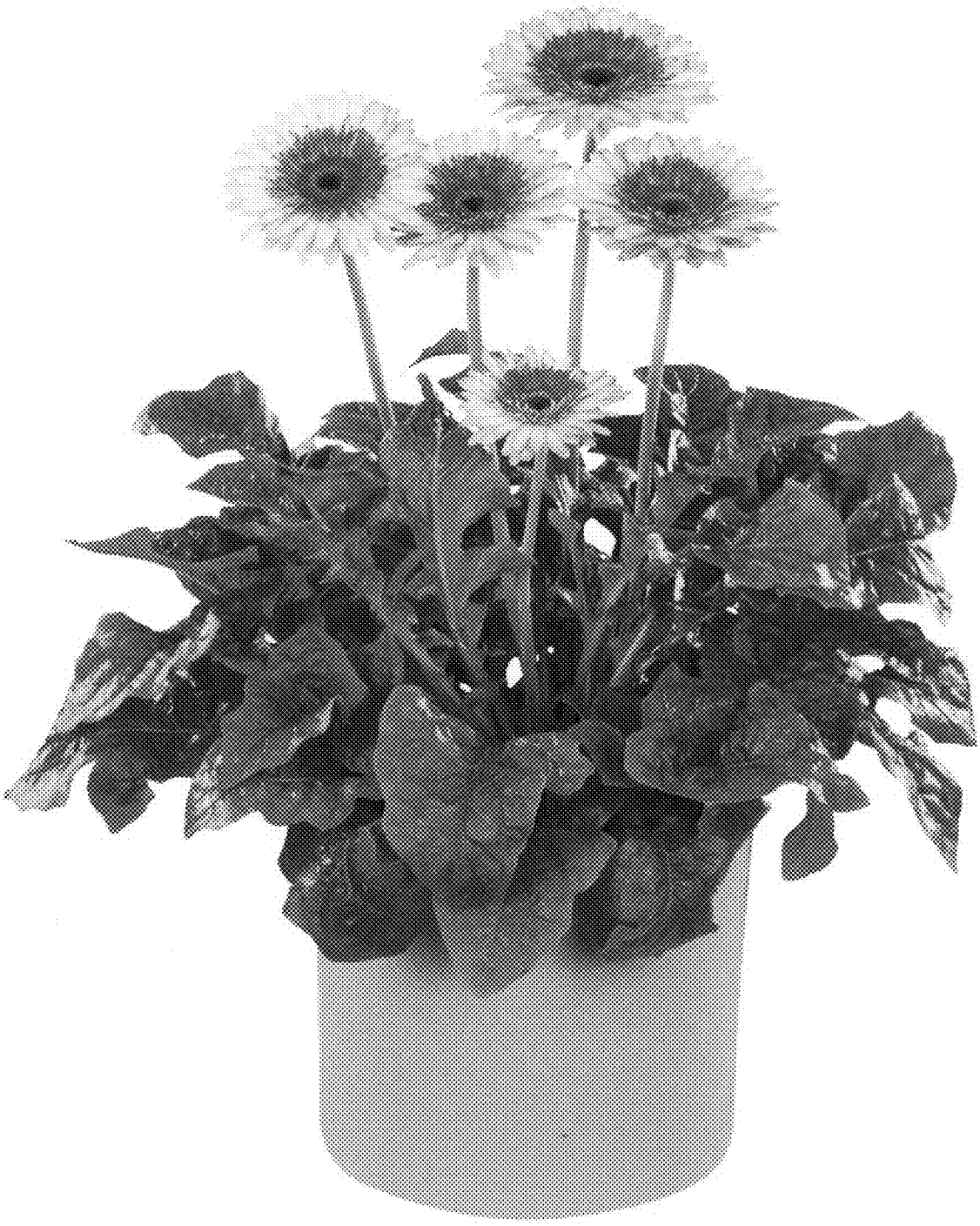

* * * * *